US006323182B1

United States Patent
Linden et al.

(12)

(10) Patent No.: US 6,323,182 B1
(45) Date of Patent: Nov. 27, 2001

(54) CONCENTRATE FOR MEDICAL SOLUTION AND USE THEREOF

(75) Inventors: Torbjörn Linden, Linderöd; Lennart Jönsson, Furulund; Stefan Knutsson, Bjärred; Robert Picard, Lund, all of (SE)

(73) Assignee: Gambro AB (SE)

( * ) Notice: Subject to any disclaimer, the term of this patent is extended or adjusted under 35 U.S.C. 154(b) by 0 days.

(21) Appl. No.: 09/529,213

(22) PCT Filed: Oct. 5, 1998

(86) PCT No.: PCT/SE98/01785

§ 371 Date: Jun. 13, 2000

§ 102(e) Date: Jun. 13, 2000

(87) PCT Pub. No.: WO99/17762

PCT Pub. Date: Apr. 15, 1999

(30) Foreign Application Priority Data

Oct. 7, 1997 (SE) .................................................. 9703650

(51) Int. Cl.[7] .................................................. A61K 31/70
(52) U.S. Cl. .............................................................. 514/23
(58) Field of Search .................................................. 514/23

(56) References Cited

U.S. PATENT DOCUMENTS 5,563,149  10/1996  Jung et al. .............................. 31/435

FOREIGN PATENT DOCUMENTS

| 0 278 100 A2 | 8/1988 | (EP) . |
| 0 437 274 A1 | 7/1991 | (EP) . |
| 0 510 687 A2 | 10/1992 | (EP) . |
| 0 612 528 A1 | 8/1994 | (EP) . |
| 0 613 688 A1 | 9/1994 | (EP) . |
| 0 821 951 A1 | 2/1998 | (EP) . |

*Primary Examiner*—Elli Peselev
(74) *Attorney, Agent, or Firm*—Lerner, David, Littenberg, Krumholz & Mentlik, LLP

(57) ABSTRACT

Concentrates are disclosed for use in the preparation of infusion solutions preferably for use in dialysis including gluconic acid and glucose in amounts such that upon dilution with an aqueous solution in a ratio of at least about 1:150, the concentration of the gluconic acid is at least about 600 mmol/l and the concentration of the glucose is at least about 150 g/l.

8 Claims, 7 Drawing Sheets

GA 1:200

GA 1:400

GA 1:400+glu

CONCENTRATE FOR MEDICAL SOLUTION AND USE THEREOF

FIELD OF THE INVENTION

The present invention relates to a concentrate for preparing a medical solution, such as a dialysis solution intended for hemodialysis, hemodifiltration, hemofiltration or peritoneal dialysis. More particularly, the present invention relates to a concentrate comprising glucose and an acid.

BACKGROUND OF THE INVENTION

A concentrate may be a solution in water of one or more substances, which solution is intended to be diluted with water in a desired ratio, such as 1:35.

A concentrate may alternatively be in powder form, for example comprising sodium bicarbonate in powder form, which concentrate is intended to be dissolved in water, and then diluted. Such dissolution may take place in a separate process, so that all of the powder is dissolved before dilution. The dissolution may also take place on-line by passing water through a bed of powder in order to produce a solution to then be diluted. The powder can be a single component, such as sodium bicarbonate or sodium chloride, or a mixture of components, such as sodium chloride, potassium chloride, magnesium chloride, calcium chloride, etc.

It is conventional during hemodialysis to prepare the dialysis solution in situ by mixing one or more concentrates with water in a dialysis machine. The dialysis machine controls the mixing so that the correct composition of the prepared dialysis solution is attained.

A dialysis machine is described in European Application No. 278,100 for the preparation of a dialysis solution starting from one or more concentrates in powder form and one or more concentrates in liquid form. The concentrates are diluted with pure water obtained from a water purifier, such as an RO-unit (reverse osmosis unit)

The dialysis machine prepares a dialysis solution comprising sodium, bicarbonate, potassium, calcium, magnesium, chloride and acetate ions in suitable concentrations, as well as possibly glucose and other ions, all being dissolved in water. The concentrations of the ions in the dialysis solution are generally mirror images of the corresponding concentrations in blood, where the mirror line is the normal concentration of the ions in blood. Thus, if an ion concentration is increased in the blood over the normal concentration, the ion concentration in the dialysis solution is decreased in relation to the normal concentration. The pH of the solution is adjusted to about 7.1 to 7.4. A typical composition of the dialysis solution is the following:

| | |
|---|---|
| sodium ions | 130–150 mM |
| bicarbonate ions | 20–40 mM |
| potassium ions | 2–5 mM |
| calcium ions | 0–5 mM |
| magnesium ions | 0–5 mM |
| glucose | 0–0.2% |
| acetate ions | 3–4 mM |
| (as well as chloride ions) | |

As is apparent from the above table, in addition to pure water, there are two substances which are present in the prepared dialysis solution in large quantities, namely sodium ions and bicarbonate ions. In the above-mentioned publication, European Application No. 280,100, at least one of these bulk substances is provided by the machine, starting from powder concentrate provided in one or more columns.

The remaining substances are supplied from a fluid concentrate which primarily comprises potassium, calcium and magnesium ions, and possibly glucose. This concentrate further comprises an acid to balance the pH value for the bicarbonate so that the final dialysis solution has a physiological pH value of about 7.1 to 7.4. Normally, acetic acid (acetate ions) is used. Since these substances are present in relatively small quantities, the solution can be very concentrated.

A concentrate is described in European Application No. 613,688 having a degree of concentration of between about 1:120 and 1:250, i.e. it is intended to be diluted with water in that ratio. It is said to comprise sodium chloride, potassium chloride, calcium chloride, magnesium chloride, hydrochloric/acetic acid and glucose. The concentrate is to be combined with a basic concentrate, which comprises the two substances which are present in large quantities, namely sodium and bicarbonate ions, derived from sodium chloride, and sodium bicarbonate. Moreover, the basic concentrate comprises sodium acetate. Sodium acetate is described as being mixed in the basic concentrate because the addition of sodium acetate prevents precipitation of bicarbonate by complex formation between acetate and bicarbonate ions. The highly concentrated concentrate is used as a treatment individualisation concentrate. This is possible since the concentrate is used in small quantities, normally less than about one liter per treatment. Many different compositions of the individualisation concentrate can be stored in a limited storage space. The highly concentrated concentrate has a very high salt concentration (ionic strength) and is viscous.

During experimentation with a highly concentrated concentrate having a degree of concentration of 1:400, comprising, among other things, glucose and 1200 mM (mmole/liter) acetic acid (undiluted), we discovered that, after one week's storage, the acetate ion concentration was reduced markedly; i.e., by more than 5%. Accordingly, the concentrate did not comply with the information on the label that it contained 3 mM (mmol/l) acetate after dilution in the ratio of 1:400 and with a margin of error of ±5%. In addition, the reduction in the acetic concentration indicated that some other substance had formed, probably by reaction with, or through decomposition of, glucose. Such substance may have an influence upon the patient who is undergoing dialysis.

During continued experiments, it appeared that there is probably an interaction or reaction between acetic acid and glucose causing the reduction in acetate concentration and also of glucose concentration. Accordingly, the concentration of acid was reduced during storage, which may result in raising the pH value of the final prepared solution to an unacceptable level.

The concentration values which are present in the concentrate are about 1.2 M acetic acid (or another acid) and about 2.2–4.4 M glucose at a concentration of 1:400, which results in 3 mM acetic acid and 0.1–0.2% glucose in the finally prepared dialysis solution.

One object of the present invention is to provide a concentrate for dilution with a medical solution, in which the acid concentration is not reduced during storage.

Another object of the present invention is to provide a concentrate for a medical solution which lacks acetate ions, since a great number of patients have developed intolerance to acetate ions.

Yet another object of the present invention is to provide a concentrate for a medical solution, comprising a physiologically acceptable aid for replacing the conventionally used acetic acid.

SUMMARY OF THE INVENTION

In accordance with the present inventions, these and other objects have now been realized by the invention of a concentrate for use in the preparation of an infusion solution comprising gluconic acid and glucose in amounts such that upon dilution with an aqueous solution in a ratio of at least about 1:150 the concentration of the gluconic acid is at least about 600 mmol/l and the concentration of the glucose is at least about 150 g/l. In a preferred embodiment, the gluconic acid and glucose are present in amounts such that upon dilution with an aqueous solution in a ratio of at least about 1:200 the concentration of the gluconic acid is at least about 800 mmol/l and the concentration of the glucose is at least about 200 g/l. In a most preferred embodiment, the gluconic acid and glucose are present in amounts such that upon dilution with an aqueous solution in a ratio of at least about 1:400, the concentration of the gluconic acid is at least about 1600 mmol/l and the concentration of the glucose is at least about 400 g/l.

In accordance with a preferred embodiment of the concentrate of the present invention, the infusion solution comprises a dialysis solution for use in hemodialysis, hemodiafiltration, hemofiltration or peritoneal dialysis.

In accordance with another preferred embodiment of the concentrate of the present invention, the concentrate is substantially free of acetate ions.

In accordance with one embodiment of the concentrate of the present invention, the concentrate includes sufficient water to provide an infusion solution in a ratio of at least about 1:150. Preferably, the concentrate includes sufficient water to provide an infusion solution in a ratio of at least about 1:200.

In accordance with another embodiment of the concentrate of the present invention, the gluconic acid is provided in the concentrate by dissolving powdered glucono-lactone in water.

During experimentation with other acids, we have thus discovered, quite surprisingly, that the abovementioned reduction of the acetic acid and glucose concentrations does not occur if gluconic acid is used instead of acetic acid. More or less the same effect also occurs with other saccharic acids such as glycuronic acid, glucaric acid, etc. The same effect can also be attained from sodium gluconate together with hydrochloric acid, due to the fact that gluconic acid is formed by the reaction of sodium gluconate and hydrochloric acid. Gluconic acid ($C_6H_{12}O_7$) can also be obtained by dissolving gluconolactone ($C_6H_{10}O_6$) in water, as described further below.

In accordance with the present invention, by replacing the conventionally used acetic acid, which contains acetate ions, with gluconic acid, even patients with acetate ion intolerance can be treated with a medical solution obtained according to this invention.

Gluconic acid has previously been used in connection with peritoneal dialysis, see European Patent No. 612,528, as an osmotic agent, i.e. as (partial) replacement for glucose. In that European patent, it is disclosed that gluconic acid can totally or partially replace glucose, i.e. mixtures of gluconic acid and glucose are used. Those concentrations which are mentioned are between 75 and 250 mM of the added or combined concentrations of gluconic acid and glucose.

In the present invention, the demonstrated effect of reduction of the acetic acid and glucose concentrations arises at considerably higher concentrations. Thus, at a degree of concentration of 1:400, the combined concentrations of glucose and gluconic acid are from about 3.4 to 5.6 M. At 250 mM, the effect according to the present invention is hardly detectable. Nowhere in European Patent No. 612,528 is it mentioned that gluconic acid should have any favorable effect on the stability of glucose.

Gluconic acid is a substance which is present in the body and may be decomposed in the body. Accordingly, it should not cause any damage or be accumulated in the body.

Gluconic acid is a somewhat stronger acid than acetic acid. In order to thus have the same effect as 3 mM acetic acid, referred to as the diluted dialysis solution, a somewhat higher concentration of gluconic acid is therefore necessary, such as from about 4 to 5 mM, probably primarily due to formation of lactones which are converted to gluconic acid at an acceptable rate only when the pH value reaches about 9.

Accordingly, there is provided, according to the present invention, a concentrate for use in the preparation of an infusion solution or a medical solution for hemodialysis, hemodiafiltration, hemofiltration or peritoneal dialysis, comprising gluconic acid. The concentrate may further comprise glucose.

Gluconic acid may replace the conventional use of acetic acid, which means that a concentrate could be produced which lacks acetate ions.

The concentrate is intended to be diluted with water or an aqueous solution in a ratio of at least about 1:150 and comprises at least about 150 g/l glucose and at least about 600 mmol/l gluconic acid.

The present invention also comprises the use of a concentrate comprising gluconic acid and glucose for the preparation of a medical infusion solution, whereby the solution is diluted with water in a ratio of at least 1:150.

According to another aspect of the present invention, it comprises use of a concentrate comprising gluconic acid and possibly glucose, for the preparation of a medical solution intended for hemodialysis, hemodifiltration, hemofiltration or peritoneal dialysis, whereby the concentrate is diluted with water and mixed with a solution comprising sodium bicarbonate and in which gluconic acid is used to adjust the medical solution to a physiological pH value of between about 7.1 and 7.4.

The present invention will be described in more detail below with reference to the following detailed description which, in turn, refers to the attached drawings. Further objects, features and advantages of the present invention will thus be apparent from the following description.

DETAILED DESCRIPTION

Figure 1:
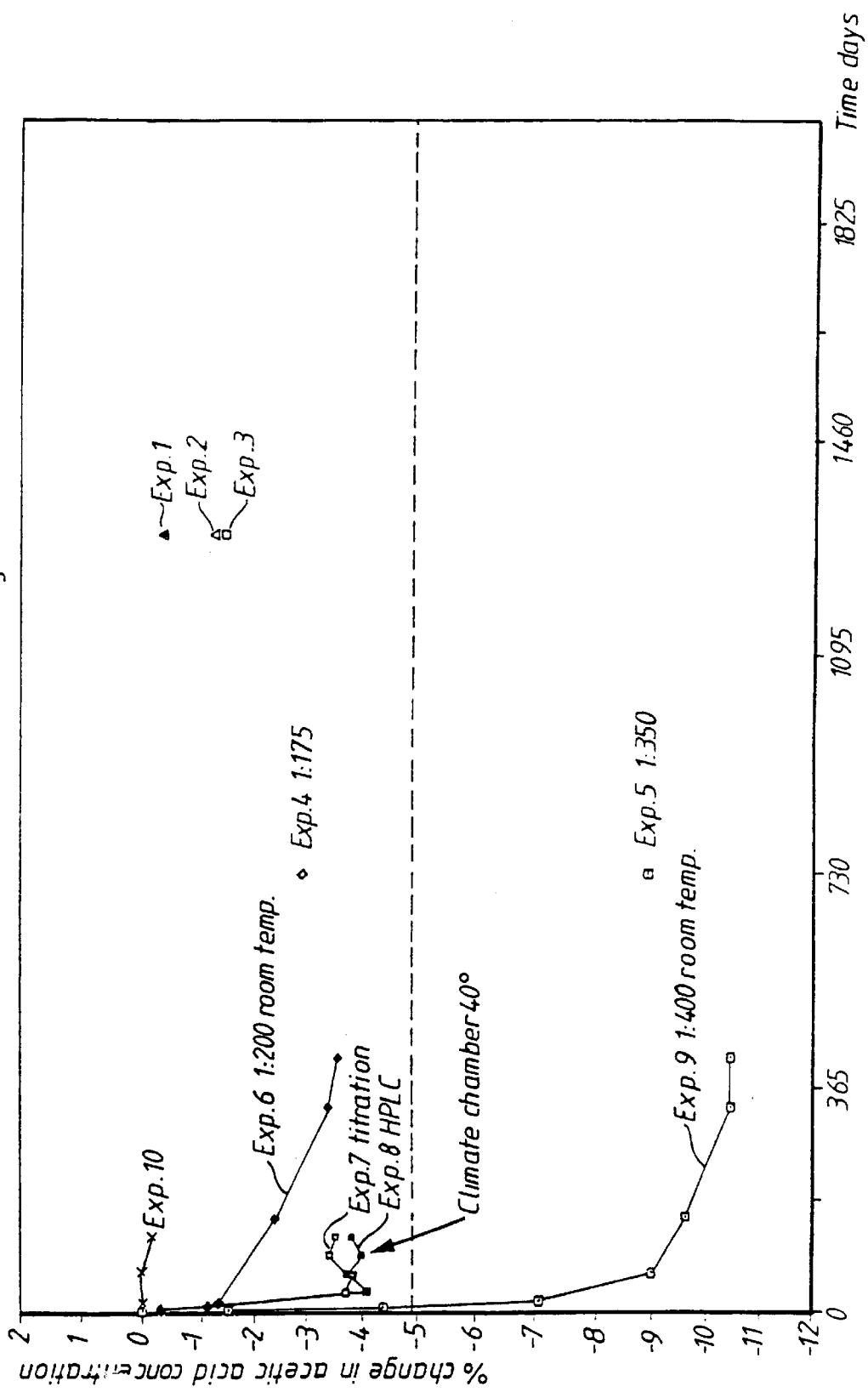
FIG. 1 is a graphical representation in which the reduction in concentration is shown as a function of time for different degrees of concentration and at different temperatures.

FIG. 1 is a diagram which includes a summary of the results of Experiments 1–10, as follows:

EXPERIMENTS 1, 2 AND 3

We have analyzed previously manufactured concentrates of a normal composition for hemodialysis and having the following intended composition after dilution:

| | |
|---|---|
| sodium | 140 mM |
| potassium | 2 mM |
| calcium | 1.75 mM |
| magnesium | 0.5 mM |
| glucose | 0.1% or 0.2% |
| acetate ions | 3 or 4 mM |

In the absence of any indications to the contrary, all of these concentration values refer to the concentration values in the finally diluted solution. The concentration values in the above disclosed concentrate are thus 35 times greater than the given values. In this manner, it is easier to compare concentrates with different degrees of concentration which are intended to result in the same concentration in the final solution.

These concentrates had been stored for 3.5 years and were analyzed for the concentration of acetic acid. The measurement points in the diagram are marked with a solid triangle for Experiment 1: 0.1% glucose, 3 mM HAc, a hollow triangle for Experiment 2: 0.2% glucose, 3 mM HAc and a hollow square for Experiment 3: 0.2% glucose, 4 mM HAc.

As is apparent from FIG. 1, the concentration of acetic acid is unchanged at 0.1% glucose and reduced at 0.2% glucose, to the extent of just under 2% at the maximum. These measured values lie within the tolerance limits for such concentrates and may be caused by differences during manufacture. We were unable to test these concentrates for shorter storage periods. However, we surmise that the deviations from the initial values would be less if the concentrates were stored for a shorter period.

EXPERIMENTS 4 AND 5

We have also analyzed liquid concentrates with the above-described composition, but without the sodium chloride, in the case where sodium chloride is produced by the dialysis machine starting from a powder concentrate. We have tested two different degrees of concentration, namely 1:175 in Experiment 4 and 1:350 in Experiment 5. The concentrates had the following composition, multiplied by 175 and 350, respectively:

| | |
|---|---|
| potassium | 2 mM |
| calcium | 1.75 mM |
| magnesium | 0.5 mM |
| glucose | 0.1% |
| acetate ions | 3 mM |

The 1:175 and 1:350 concentrates were tested after 2 years of storage, and the result is illustrated in FIG. 1, using a diamond for Experiment 4, 1:175, and a hollow dotted square for Experiment 5, 1:350. As is clearly apparent, the reduction in the acetic acid concentration for the concentration 1:175 is about 3%, which is within the tolerance limits. For the double concentration 1:350, there is a reduction of about 9%, which is outside of the tolerance limits.

EXPERIMENTS 6, 7, 8 AND 9

We have performed a test series with concentrates having degrees of concentration of 1:200 and 1:400 which were manufactured and continuously monitored during a period of just over one year. The concentrates had the same composition as those used for experiments 4 and 5, except that they were multiplied with the given degrees of concentration.

The 1:200 concentrate in Experiment 6, denoted on FIG. 1 by solid diamonds, demonstrates a continuous reduction of the acetic acid concentration that seems to level out at a reduction of just below 4%.

The same applies for two experiments; namely, Experiment 7, indicated by hollow small squares, and Experiment 8, indicated by filled small squares, with the same composition but aged in a climatic chamber at 40° C. As is apparent from FIG. 1, Experiments 7 and 8 reach equilibrium at a reduction of about 4% after about 2 months. The curve of Experiment 7 was obtained by means of titration and the curve of Experiment 8 was obtained by HPLC chromatography. The differences lie within the error tolerances of the methods.

We have also manufactured a concentrate with a degree of concentration of 1:400, Experiment 9 indicated by hollow squares with a dot, which was followed for slightly more than one year. Here the situation, as illustrated in FIG. 1, is quite clear, namely that the acetic acid concentration reduces rapidly during the first weeks and then levels out at a reduction of about 10.5%.

EXPERIMENT 10

We have also performed experiments with concentrates without glucose having a degree of concentration of 1:400. As is apparent from FIG. 1, where Experiment 10 is indicated by crosses, no marked reduction of acetic acid concentration is detected.

The combined observations from the various experiments is quite clear. The acetic acid concentration reduces in all concentrates. The reduction is dependent on the degree of concentration of the solution. This effect has not been observed in the literature.

We have also been able to determine that the glucose concentration reduces in proportion to the reduction of the acetic acid concentration. This causes us to assume that the acetic acid reacts with glucose and forms a reaction product.

We have unexpectedly discovered that if the acetic acid is replaced by gluconic acid, the above reduction of the acid concentration and the glucose concentration is not observed, as can be seen in the following experiments.

FIGS. 2–8 are diagrams of the concentration of gluconic acid and the pH values, respectively, for concentrates with the following composition:

| | |
|---|---|
| potassium | 2 mM |
| calcium | 1.75 mM |
| magnesium | 0.5 mM |
| glucose | 0% or 0.1% |
| gluconic acid | 4 mM |

EXPERIMENTS 11 AND 12

Figure 2:
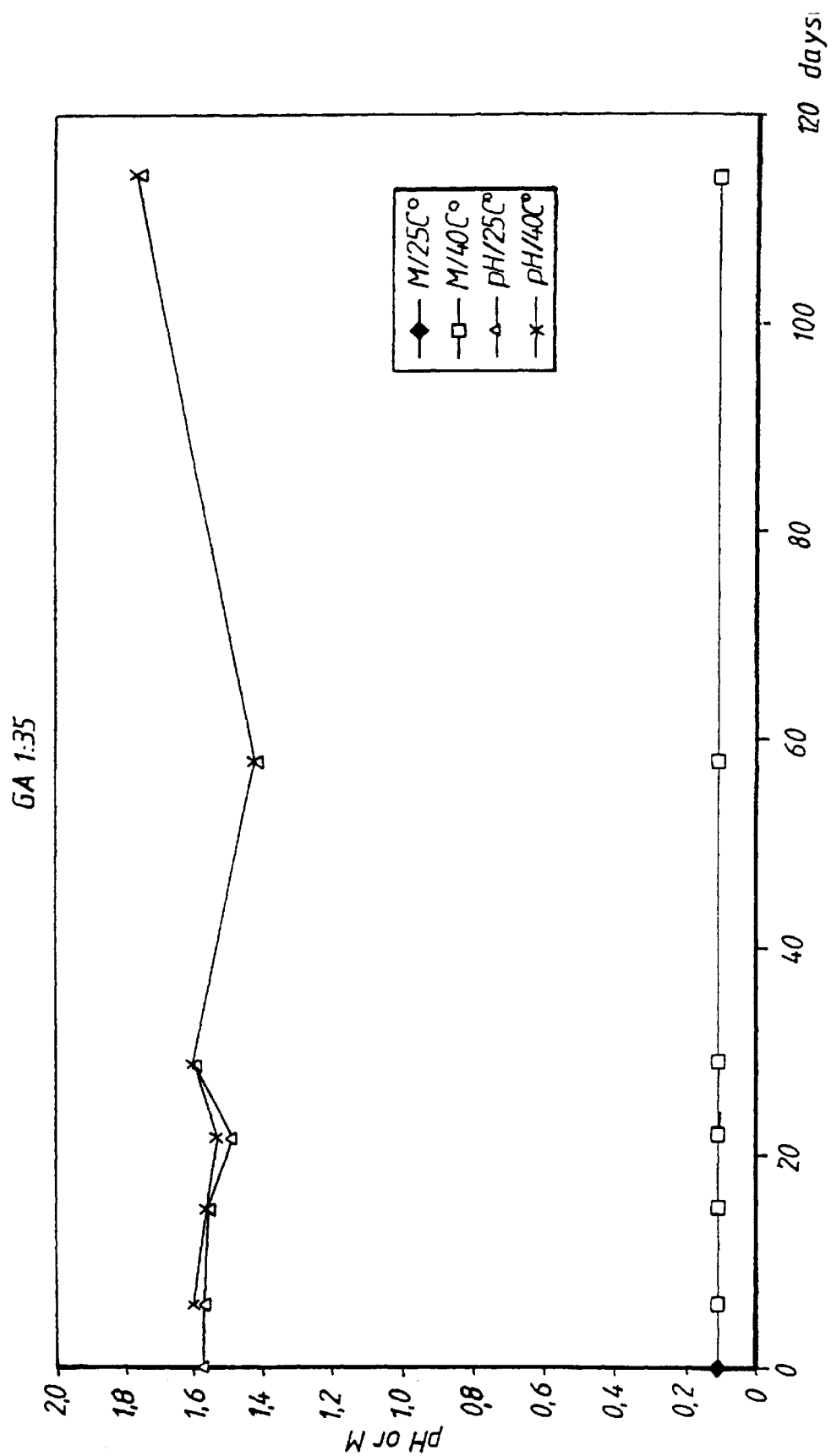
FIG. 2 is a graphical representation in which the concentration of gluconic acid is shown as a function of time for different degrees of concentration and with and without glucose.
Figure 3:
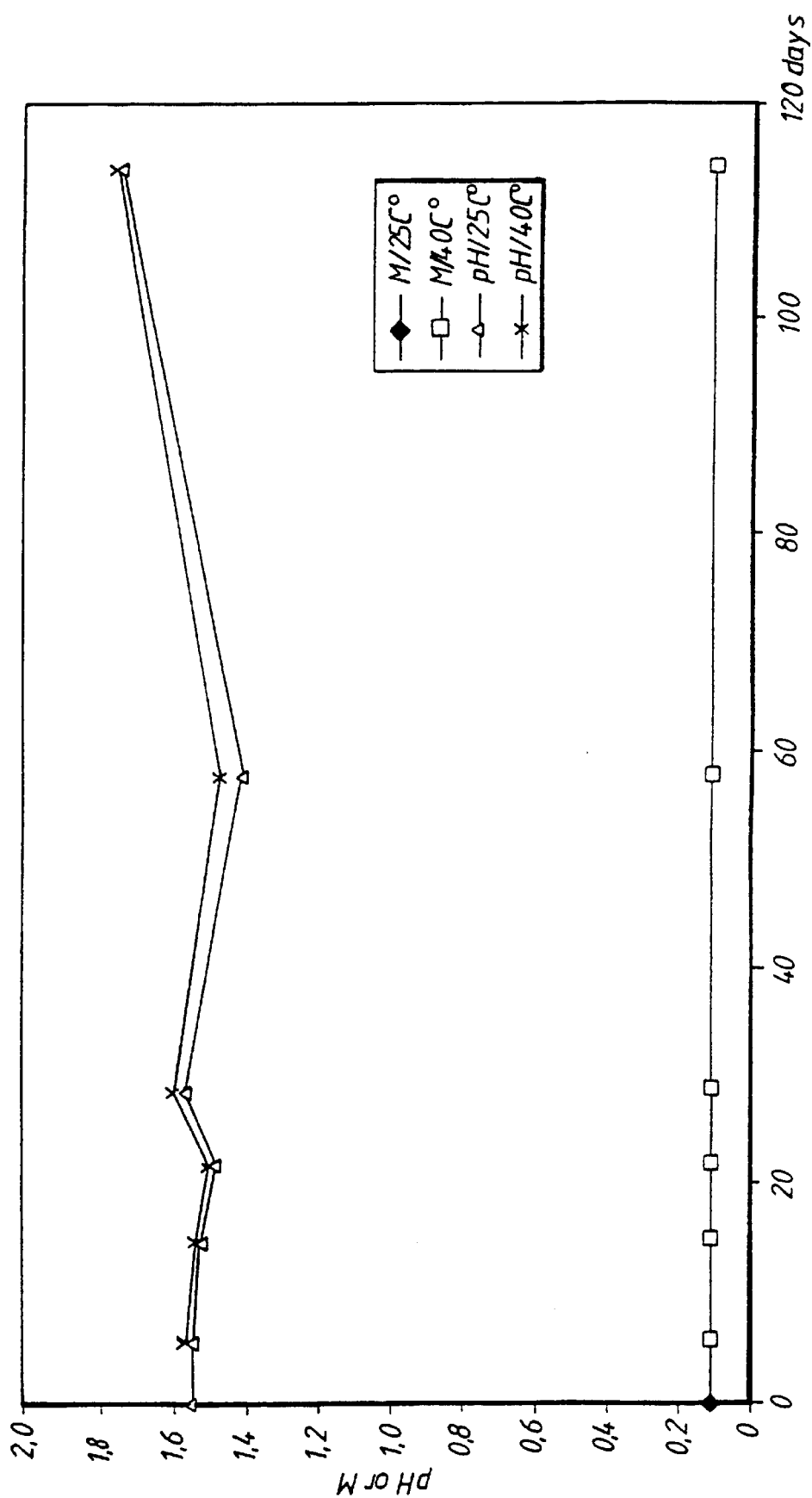
FIG. 3 is a graphical representation in which the concentration of gluconic acid is shown as a function of time for different degrees of concentration and with and without glucose.

In experiments 11 and 12, FIGS. 2 and 3, a concentrate with a degree of concentration of 1:35, i.e. a "conventional" concentrate, was used. The concentrate further comprises sodium chloride with a concentration of 140 mM (times 35). Experiment 11 is without glucose and experiment 12 is with 0.1% glucose. Two parallel trial series are run, one in which the concentrates are stored at 25° C. and the other in which the concentrates are stored at 40° C. Since ageing takes place more quickly at higher temperatures, a difference between the two concentrates should quickly arise if any reaction takes place.

As is seen from FIGS. 2 and 3, no differences are observed. The concentration of the gluconic acid was measured by means of titration (square and diamond denoted by M/25C and M40C in FIGS. 2 and 3) and by measurement of the pH value (triangle and cross denoted by pH/25C and pH/40C in FIGS. 2 and 3). As is apparent from FIGS. 2 and 3, the concentration of gluconic acid is constant at about 0.105 M. Furthermore, the pH value is relatively constant at pH=1.6. The variations which are apparent in FIGS. 2 and 3, and also from the following diagrams, are believed to be due to calibration of the pH meter.

EXPERIMENTS 13 AND 14

Figure 4:
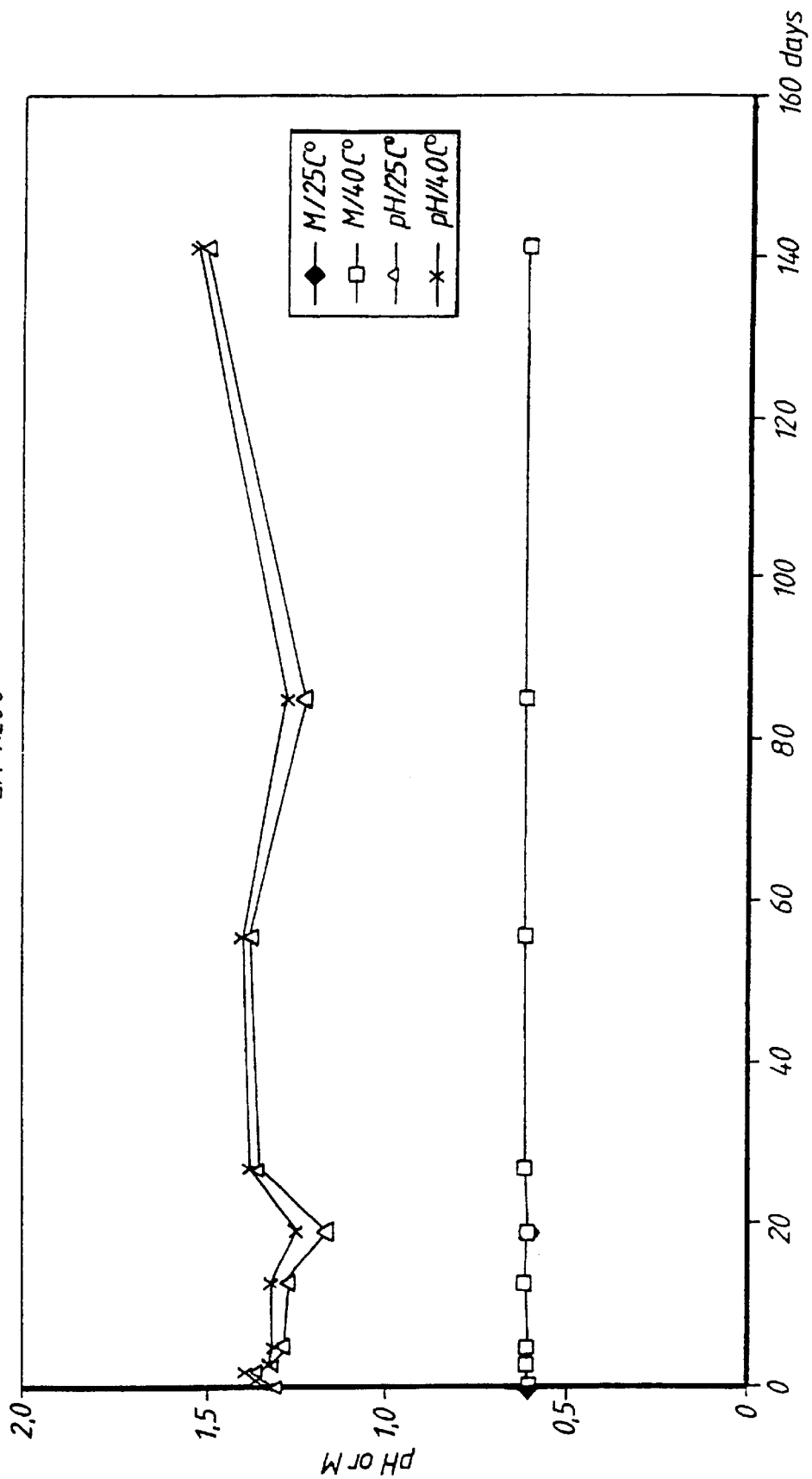
FIG. 4 is a graphical representation in which the concentration of gluconic acid is shown as a function of time for different degrees of concentration and with and without glucose.
Figure 5:
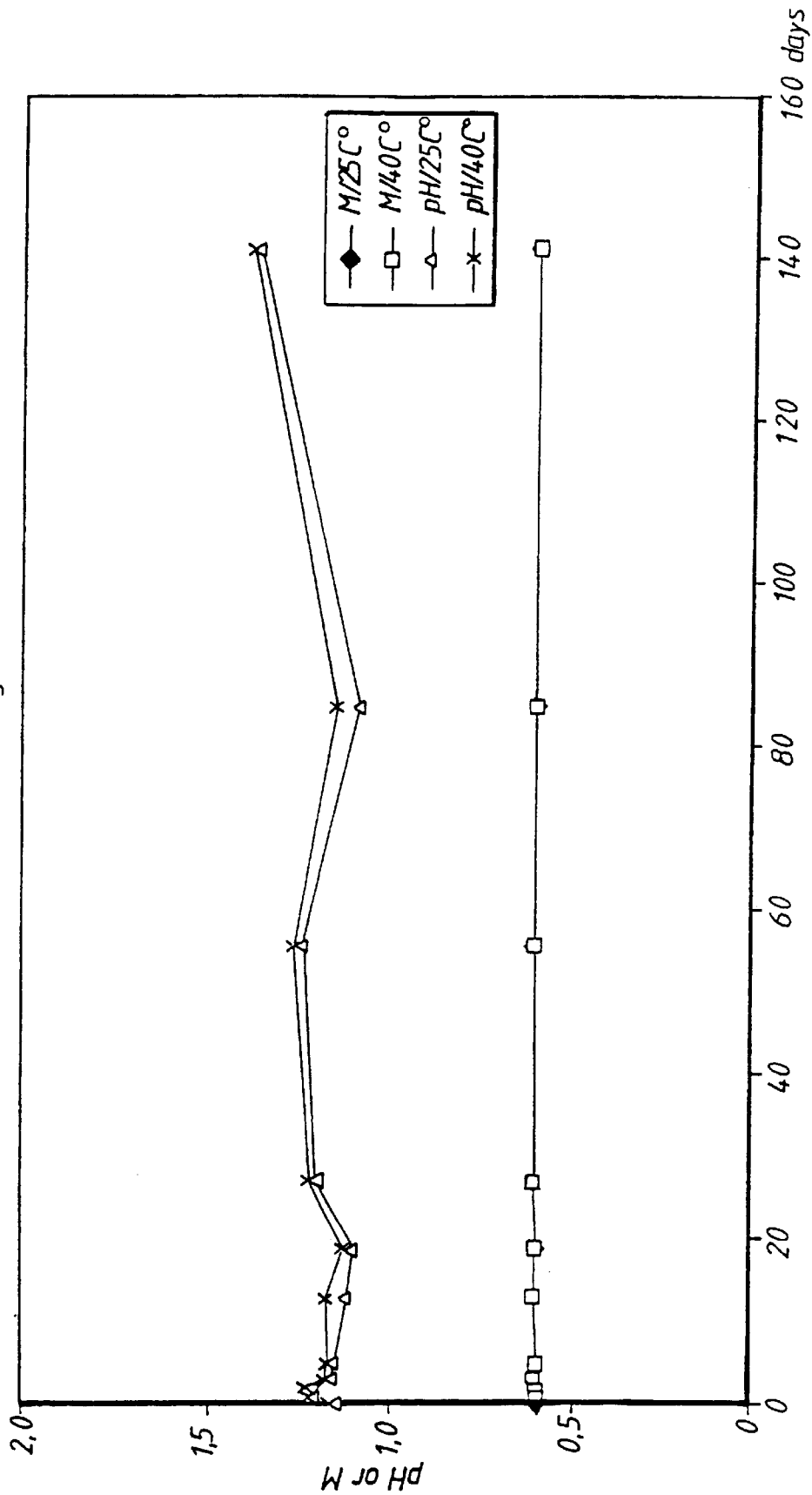
FIG. 5 is a graphical representation in which the concentration of gluconic acid is shown as a function of time for different degrees of concentration and with and without glucose.

As illustrated in FIGS. 4 and 5, the same experiments were performed as in experiments 11 and 12, with a degree of concentration of 1:200 and without sodium chloride.

It is apparent from these figures that no change occurs in the concentration of gluconic acid which is constant at 0.6 M. The pH values are also relatively constant.

EXPERIMENTS 15 AND 16

Figure 6:
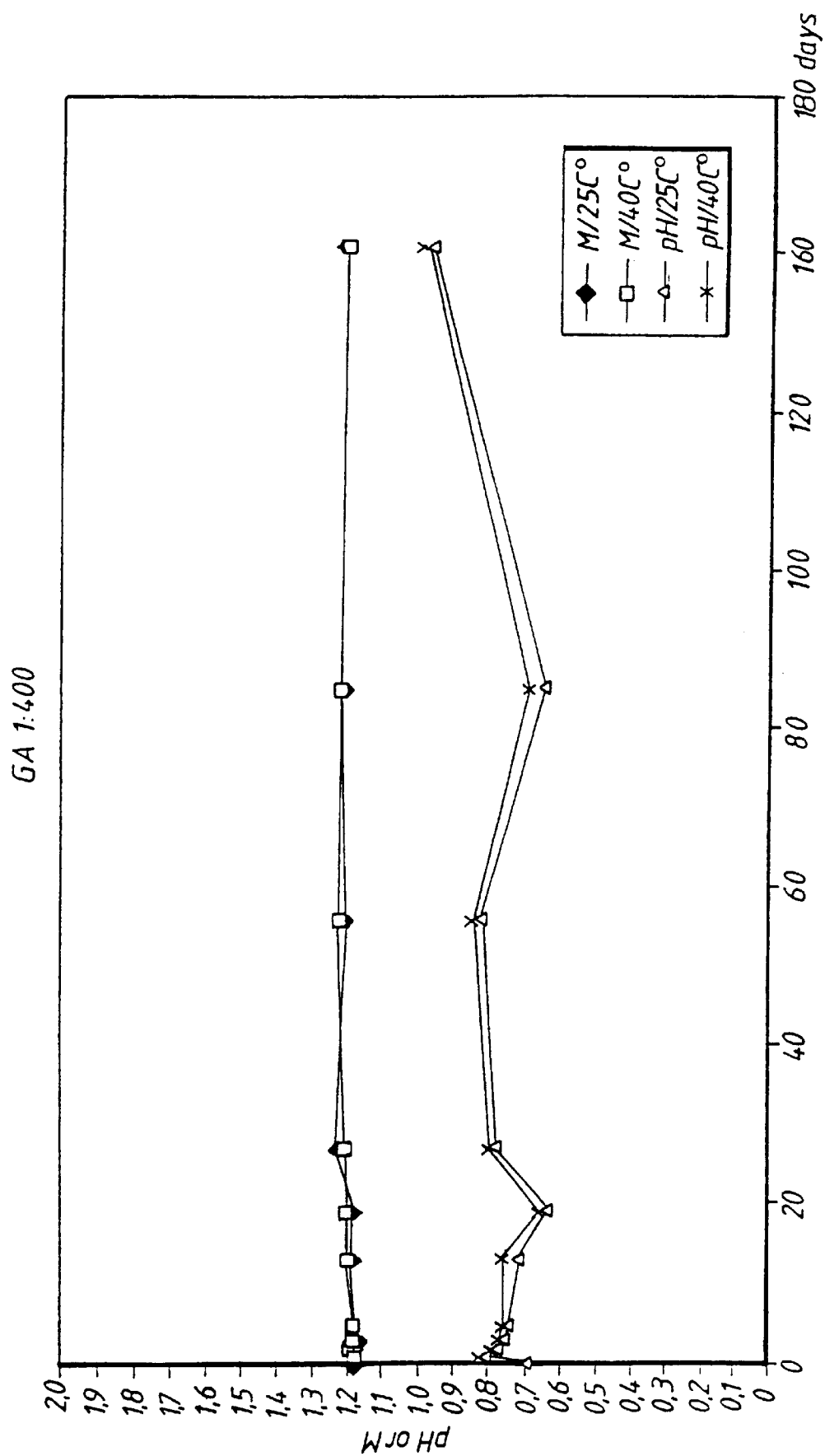
FIG. 6 is a graphical representation in which the concentration of gluconic acid is shown as a function of time for different degrees of concentration and with and without glucose.
Figure 7:
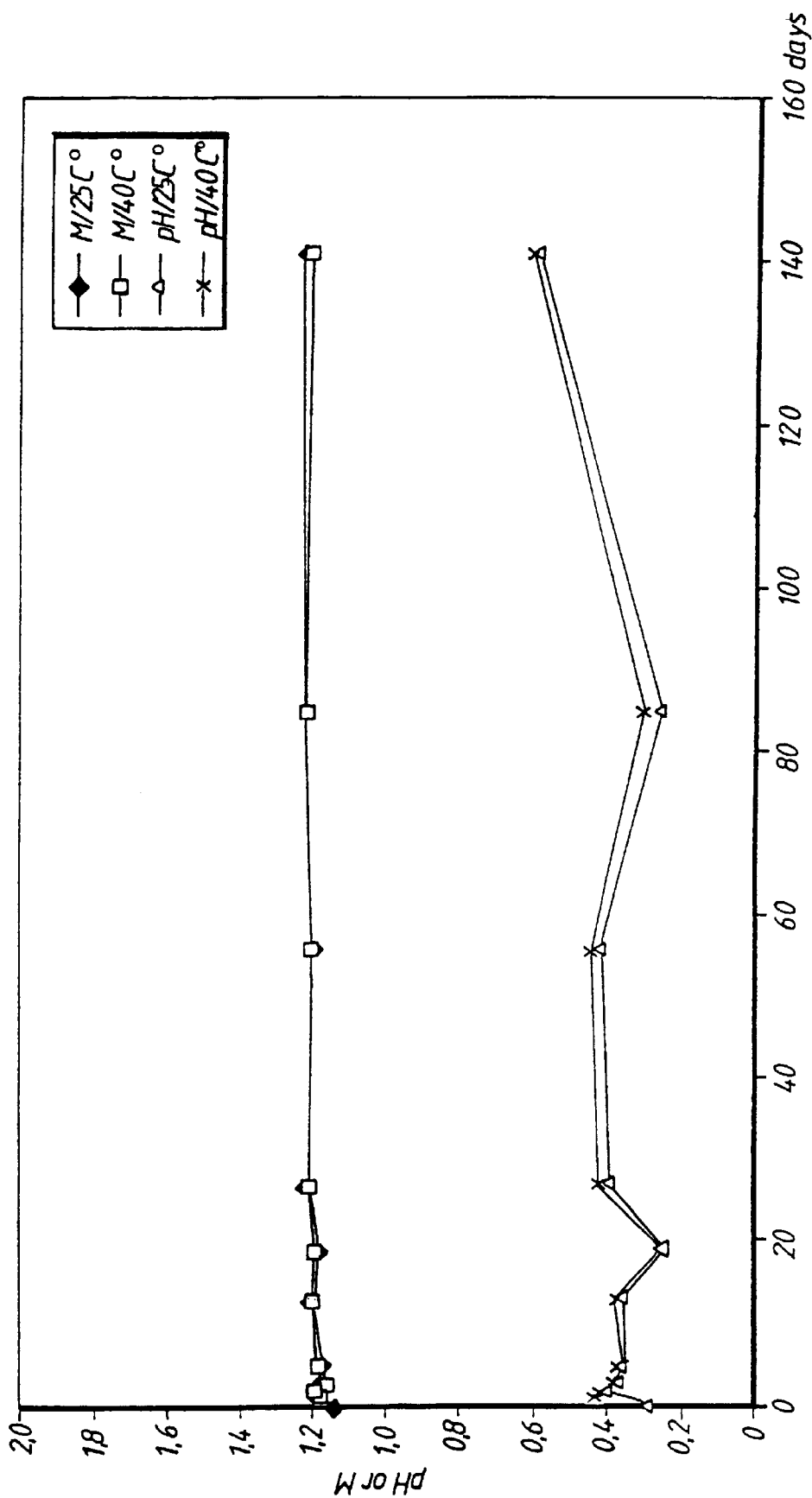
FIG. 7 is a graphical representation in which the concentration of gluconic acid is shown as a function of time for different degrees of concentration and with and without glucose.

As illustrated in FIGS. 6 and 7, the same experiments were performed as in experiments 13 and 14, with a degree of concentration of 1:400.

Again, it is apparent from the diagrams that substantially no change occurs in the concentration of gluconic acid which is constant at 1.2 M (undiluted). The pH values are also relatively constant.

It is to be noted that the pH value in FIG. 7, where glucose is added, is clearly lower than in FIG. 6, without glucose. We believe that this difference is not an actual difference but instead is due to glucose affecting the pH electrode. As is apparent, the titrated concentration (M) is constant and of the same magnitude in FIGS. 6 and 7.

Our measurements over a long period and documented in Experiments 11–16 show that the gluconic acid retains a stable concentration and does not appear to react with glucose. Accordingly, both the acid concentration and the glucose concentration are retained.

It should be noted that a somewhat greater quantity of gluconic acid is required as compared to acetic acid in order to obtain the same effect when mixing a dialysis solution starting from concentrates.

We have not been able to find any reason to suspect that any unidentified substance is produced which may have potentially damaging effect on a patient who is treated using this concentrate (after dilution) during dialysis or infusion.

Gluconic acid can be obtained on the market in the form of 50% solution. However, we prefer to use glucono-delta-lactone ($C_6H_{10}O_6$) which can be obtained in powder form and in pure form. When dissolved in water, gluconolactone is substantially immediately hydrolysed to gluconic acid.

Gluconic acid is naturally occurring in the body. We have been unable to evidence any damaging effect on the body from the use of gluconic acid during dialysis.

According to the present invention, the conventionally used acetic acid is replaced by gluconic acid. The gluconic acid, or more precisely gluconate, can also act as a buffer, and thus replace lactate during peritoneal dialysis.

Gluconic acid can also be produced in situ by mixing sodium gluconate with hydrochloric acid, whereby gluconic acid is formed. It is also possible to use other salts comprising gluconate, such as potassium gluconate, calcium gluconate and magnesium gluconate, since these cations, potassium, calcium and magnesium ions, normally are included in a dialysis solution. In other types of solutions, other salts may be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A concentrate for use in the preparation of a dialysis solution comprising gluconic acid and glucose in amounts such that upon dilution with an aqueous solution in a ratio of at least about 1:150 the concentration of said gluconic acid is at least about 600 mmol/l and the concentration of said glucose is at least about 150 g/l.

2. A concentrate for use in the preparation of a dialysis solution comprising gluconic acid and glucose in amounts such that upon dilution with an aqueous solution in a ratio of at least about 1:200 the concentration of said gluconic acid is at least about 800 mmol/l and the concentration of said glucose is at least about 200 g/l.

3. A concentrate for use in the preparation of a dialysis solution comprising gluconic acid and glucose in amounts such that upon dilution with an aqueous solution in a ratio of at least about 1:400 the concentration of said gluconic acid is at least about 1600 mmol/l and the concentration of said glucose is at least about 400 g/l.

4. A concentrate according to claim 1, 2 or 3 wherein said dialysis solution comprises a dialysis solution for use in hemodialysis, hemodiafiltration, hemofiltration or peritoneal dialysis.

5. The concentrate of claim 1, 2 or 3 substantially free of acetate ions.

6. The concentrate of claim 1 including sufficient water to provide a dialysis solution in a ratio of at least about 1:150.

7. The concentrate of claim 6 including sufficient water to provide a dialysis solution in a ratio of at least about 1:200.

8. The concentrate of claim 1 wherein said gluconic acid is provided in said concentrate by dissolving powdered glucono-lactone in water.

* * * * *